United States Patent [19]

Sommer et al.

[11] 4,241,212
[45] Dec. 23, 1980

[54] CHEMICAL AGENTS

[75] Inventors: Harold Z. Sommer, Havre de Grace; George E. Wicks, Jr., Baltimore, both of Md.

[73] Assignee: The United States of America as represented by the Secretary of the Army, Washington, D.C.

[21] Appl. No.: 673,248

[22] Filed: Sep. 29, 1967

[51] Int. Cl.³ ............................................. C07D 213/63
[52] U.S. Cl. ...................................... 546/291; 424/263
[58] Field of Search ................ 260/296; 424/300, 263; 546/291

[56] References Cited

U.S. PATENT DOCUMENTS 3,188,955  6/1965  Brown ..................................... 102/24

Primary Examiner—Leland A. Sebastian
Attorney, Agent, or Firm—Nathan Edelberg; Robert P. Gibson; Harold H. Card, Jr.

[57] ABSTRACT

New chemical compounds, bis-quaternary carbamates, having the generic formula:

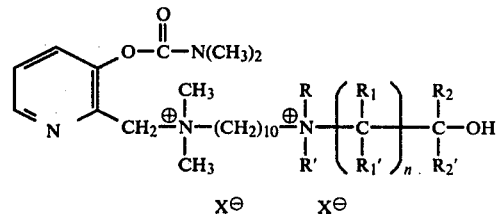

wherein R and R' are radicals selected from the group consisting of methyl, ethyl, propyl, and hydroxyethyl, $R_1$ and $R_1'$ are selected from the group consisting of hydrogen, methyl, and ethyl, n is 1 to 8, $R_2$ and $R_2'$ are selected from the group consisting of hydroxyl, hydrogen, methyl, ethyl, and propyl, and X is one equivalent of a monovalent or polyvalent anion, and having utility as toxic agents.

2 Claims, No Drawings

CHEMICAL AGENTS

DEDICATORY CLAUSE

The invention described herein may be manufactured, used, and licensed by or for the Government for governmental purposes without the payment to us of any royalty thereon.

This invention relates to the synthesis of new toxic chemical compounds which are useful as chemical warfare agents. More particularly, our invention is concerned with novel compounds produced by means of a quaternizing reaction.

The chemical agents act mostly on the peripheral cholinergic nervous system which includes the motor nerves, the preganglionic fibers, the ganglia, the postganglionic parasympathetic fibers, and neuromuscular functions. The transmission of impulses along a nerve or from nerve fibers to muscle fibers or secretory cells or from one nerve fiber to another across synapses in ganglia is thought to involve chemical changes either directly or as the source of potential differences.

Quaternary ammonium compounds in general are known to be physiologically active materials. Mainly because of their positively charged "onium" centers they are attracted by anionic sites in animal tissues, particularly those situated at cell surfaces and interfaces. They can induce physiological responses that mimic or antagonize the action of acetylcholine as a result of their interaction with the various physiological receptor sites of acetylcholine, especially those at membranes of muscle cells. They also combine with enzymes such as acetylcholinesterase, other esterases, acetylcholineacetylase, etc., thus inhibiting their participation in the biological processes.

One of the significant anatomical differences between the neuromuscular junctions and other acetylcholine receptive sites is the absence of a membrane barrier or a sheath such as envelops the ganglia. The comparative ease of accessibility of the neuromuscular junctions to "onium" compounds contributes to their relatively fast onset of action and partly explains why in many instances relatively small doses suffice to evoke physiological actions that modify or interrupt normal neuromuscular impulse transmission.

Depending on their chemical structures different quaternary compounds interfere with the mechanism of impulse transmission in different manners and the final physiological effects can vary considerably. Some quaternary ammonium compounds are used as therapeutic agents, others are known to be lethal. The magnitude, accessibility, and distribution of the positive charges in quaternary compounds are believed to be the key factors in the determination of specificity of action. Recognition of these facts explains the strikingly different physiological behavior so often observed when structurally very closely related compounds are compared. The nature of the groups attached to the quaternary nitrogens influences the distribution of the cationic charges. The length and branching of aliphatic chains and the volume and configuration of aromatic and alicyclic rings have a bearing on the ease or difficulty of approach to the specific receptor sites. Electrophilic and nucleophilic centers in the molecule will insert their inductive effects on the positive charges and can also aid in the interaction with the "esteratic sites" of various enzymes. These sites are believed to be located in close vicinity to the anionic sites of the active centers. Substitution of different functional groups influences association and hydration and may considerably change the solubilities in physiological media. In bis-quaternary and poly-quaternary compounds the distance between the electric charges must be considered. These factors contribute to govern the rate and reversibility of the chemical reactions involved and contribute to determine the final physiological responses.

Our chemical agents interfere with the normal process of neuromuscular impulse transmission and thus disrupt the propagation of impulses from nerves to muscles. We have also found these compounds to be extremely toxic at relatively low dose levels in various animals.

The object of this invention is to synthesize new lethal agents useful in chemical warfare in high yields wherein said products are well suited for industrial scale manufacture.

Other objects of and uses for the invention will in part be obvious and will in part appear hereinafter in the following detailed description thereof.

Our compounds may be employed in any munition suitable for handling a relatively non-volatile toxic agent such as bombs, shells, spray tanks, rockets, missiles, aerosol generators, and others.

In accordance with our invention the tertiary amino-function of an aliphatic aminoalcohol, such as hydroxyethyldimethylamine, was quaternized with N-(10-bromodecyl)-N-(3-dimethylcarbamoxy-α-picolinyl)-N,N-dimethylammonium bromide in a solvent, such as acetonitrile, under reflux conditions, or allowing the reaction mixture to stand for prolonged periods of time at room temperature and refluxing the reaction mixture for a relatively short period of time. After the reaction took place the solution was concentrated to a few milliliters and, on addition of a solvent, such as acetone or ethyl acetate, an oily material separated. The supernatant solvent mixture was decanted, and the remaining oil was stirred in a boiling solvent, such as acetone or ethyl acetate. The mixture was allowed to cool to room temperature, the solvent decanted, and the gummy residue dissolved in a solvent such as methanol or acetonitrile. This solution was treated with decolorizing carbon and then concentrated to a few milliliters. The concentrate was placed in an apparatus that was kept under reduced pressure. The resultant white solid material constitutes the new compounds of the present invention which may be represented by the following generic formula:

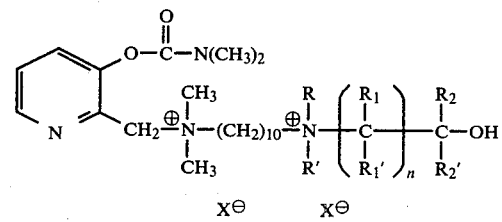

wherein X is one equivalent of a monovalent or polyvalent anion, R and R' are aliphatic radicals selected from the group consisting of methyl, ethyl, propyl, and hydroxyethyl, $R_1$ and $R_1'$ are selected from hydrogen, methyl, and ethyl, n is selected from 1–8, and $R_2$ and $R_2'$ are selected from hydroxyl, hydrogen, methyl, ethyl, and propyl.

The procedure used for the preparation of the new toxic materials is schematically shown below:

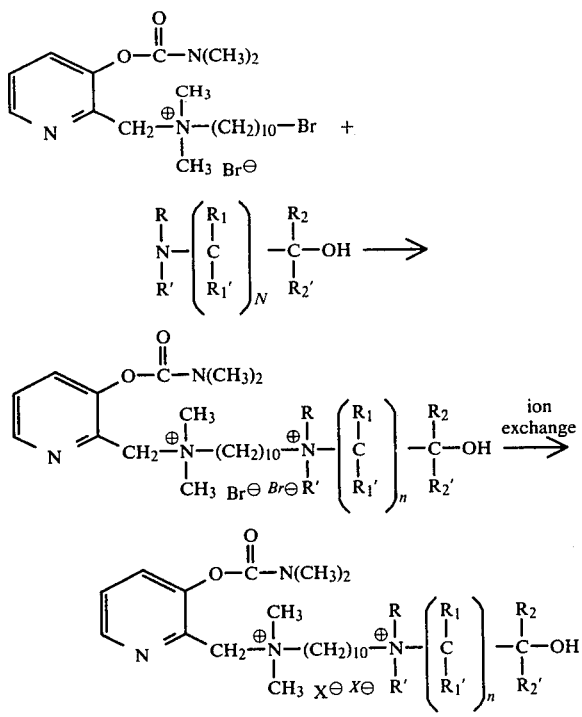

wherein X is a halide ion, preferably bromide, and R, R', R$_1$, R$_1$', R$_2$, R$_2$', and n is defined above.

If compounds are desired in which X is other than a halide ion, the above quaternary compounds are treated with the desired acid by simple exchange reactions as set forth below.

EXAMPLE 1

N-(10-Bromodecyl)-N-(3-dimethylcarbamoxy-α-picolinyl)-N,N-dimethylammonium bromide (1.05 g) and 2-dimethylaminoethanol (0.22 g) were dissolved in 10 ml of acetonitrile and refluxed for about 24 hours. The reaction mixture was then concentrated on a steam bath to about 3 ml and allowed to cool to room temperature. The addition of 50 ml of acetone caused an oily material to separate. The supernatant solvent mixture was decanted, and the remaining oil was stirred for about 15 minutes in 50 ml of boiling acetone. The mixture was allowed to cool to room temperature, the acetone decanted, and the gummy residue dissolved in 25 ml of methanol. The solution was treated with decolorizing carbon and concentrated to a few milliliters. The concentrate was placed in an apparatus that was kept under reduced pressure (about 1 mm) and at the temperature of refluxing ethyl acetate for about 5 hours. The product, 1-[N,N-dimethyl-N-(2-hydroxy)ethylammonio]-10-[N-(3-dimethylcarbamoxy-α-picolinyl)-N,N-dimethylammonio]decane dibromide, (0.87 g) was obtained as a white crystalline material.

Analysis for $C_{25}H_{48}Br_2N_4O_3$: Calcd: C, 49.0; H, 7.9; Br, 26.0. Found: C, 48.9; H, 8.0; Br, 25.9.

| Toxicity IV LD$_{50}$ | |
|---|---|
| Rabbits | Mice |
| 0.0045 mg/kg | 0.009 mg/kg |

EXAMPLE 2

N-(10-Bromodecyl)-N-(3-dimethylcarbamoxy-α-picolinyl)-N,N-dimethylammonium bromide (1.05 g) and 3-dimethylaminopropanol (0.4 g) were dissolved in 5 ml of acetonitrile and the solution was allowed to stand at room temperature for about 9 days. The reaction mixture was then refluxed for about 1 hour and cooled to room temperature. The addition of 50 ml of acetone caused an oily material to separate. The solvent mixture was decanted, and the remaining oil was stirred in 50 ml of boiling ethyl acetate for 30 minutes. After the mixture was allowed to cool to room temperature, the supernatant solvent was decanted and the gummy residue was dissolved in 15 ml of methanol. This solution was treated with decolorizing carbon and concentrated to a few milliliters. The concentrate was placed in an apparatus that was kept under reduced pressure (about 1 mm) at the temperature of boiling chloroform. The product, 1-[N,N-dimethyl-N-(3-hydroxy)-propylammonio]-10-[N-(3-dimethylcarbamoxy-α-picolinyl)-N,N-dimethylammonio]decane dibromide (1.0 g), was obtained as a deliquescent white solid.

Analysis: for $C_{26}H_{50}Br_2N_4O_3$: Calcd: C, 49.9; H, 8.0; Br, 25.5. Found: C, 50.2; H, 8.0; Br, 25.3.

| Toxicity IV LD$_{50}$ | |
|---|---|
| Rabbits | Mice |
| 0.0056 mg/kg | 0.0036 mg/kg |

EXAMPLE 3

N-(10-Bromodecyl)-N-(3-dimethylcarbamoxy-α-picolinyl)-N,N-dimethylammonium bromide (1.05 g) and di(2-hydroxyethyl) methylamine (0.6 g) were dissolved in 10 ml of acetonitrile, and the solution was refluxed for about 24 hours. The reaction mixture was then concentrated on a steam bath to about 3 ml and allowed to cool to room temperature. On addition of ethyl acetate, a viscous oily material precipitated. The supernatant solvent mixture was decanted, and the remaining gummy oil was stirred in 50 ml of hot ethyl acetate for about 30 minutes. After the mixture was allowed to cool to room temperature, the ethyl acetate was decanted and the gummy residue dissolved in 20 ml of acetonitrile. This solution was treated with decolorizing carbon and concentrated on a steam bath to a few milliliters. The concentrate was placed in an apparatus that was kept under reduced pressure (about 1 mm) for about 20 hours. The product, 1-[N,N-di(2-hydroxy)ethyl-N-methylammonio]-10-[N-(3-dimethylcarbamoxy-α-picolinyl)-N,N-dimethylammonio]decane dibromide (0.9 g), was obtained as a white deliquescent solid. Due to its extreme deliquescency, a sample of the compound was converted to and analyzed as the tetraphenylboronate salt. The above dibromide salt was dissolved in water and to this solution an aqueous solution of sodium tetraphenylboron (in molar excess) was added. The solid precipitate that formed was collected on a filter, washed a few times with water, and dried. The tetraphenylboronate salt melted between 62°–66° C.

Analysis for $C_{74}H_{90}B_2N_4O_4$: Calcd: C, 79.3; H, 8.1; N, 5.0. Found: C, 79.2; H, 8.0; N, 5.1.

| | Toxicity IV LD$_{50}$ | |
|---|---|---|
| Rabbits | | Mice |
| 0.0054 mg/kg | | 0.014 mg/kg |

Method of Preparation of N-(10-Bromodecyl)-N-(3-dimethylcarbamoxy-α-picolinyl)-N,N-dimethylammonium bromide.

A solution of 62.3 g of 2-dimethylaminoethyl-3-dimethylcarbamoxypyridine and 251 g of 1,10-dibromodecane was refluxed for about 7 days in 1 liter of anhydrous ether. The solid product that formed was collected on a filter, washed with two 200 ml portions of anhydrous ether, and dissolved in 1 liter of acetone. The acetone solution was treated with decolorizing carbon and filtered. The filtrate was concentrated under reduced pressure to approximately 200 ml. Ether was added until the solution became turbid, and the mixture was seeded and chilled overnight. The resultant crystalline product was collected and further purified by recrystallization from ethyl acetate. The pure product was dried in vacuo for about 2 hours, yielding 76 g of material, m.p. 90°–92° C.

Analysis for $C_{21}H_{37}Br_2N_3O_2$: Calcd: C, 48.2; H, 7.1; Br$^-$(ionic), 15.3; O, 6.1. Found: C, 48.2; H, 7.2; Br$^-$(ionic), 15.2; O, 6.2.

The compounds that are representative of our invention are listed below by name and chemical structure.

1-[N,N-dimethyl-N-(2-hydroxy)ethylammonio]-10-[N-(3-dimethylcarbamoxy-α-picolinyl)-N,N-dimethylammonio]-decane dibromide

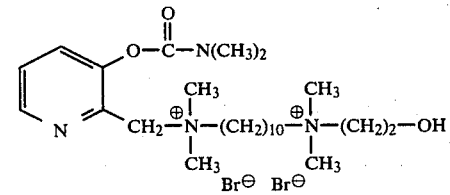

1-[N,N-dimethyl-N-(3-hydroxy)propylammonio]-10-[N-(3-dimethylcarbamoxy-α-picolinyl)-N,N-dimethylammonio]-decane dibromide.

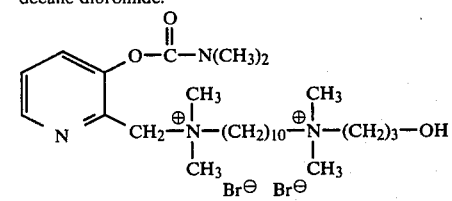

1-[N,N-dimethyl-N-(4-hydroxy)butylammonio]-10-[N-(3-dimethylcarbamoxy-α-picolinyl-N,N-dimethylammonio]-decane dibromide.

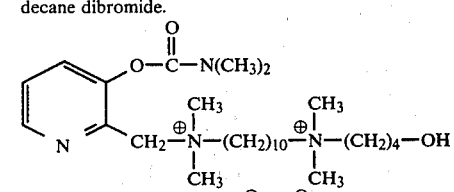

1-[N,N-dimethyl-N-(6-hydroxy)hexylammonio]-10-[N-(3-dimethylcarbamoxy-α-picolinyl)-N,N-dimethylammonio]-decane dibromide.

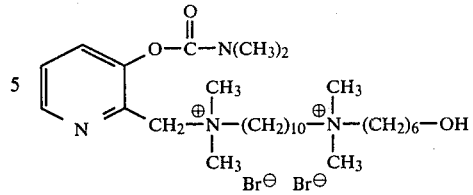

1-[N,N-dimethyl-N-(8-hydroxy)octylammonio]-10-[N-(3-dimethylcarbamoxy-α-picolinyl)-N,N-dimethylammonio]-decane dibromide.

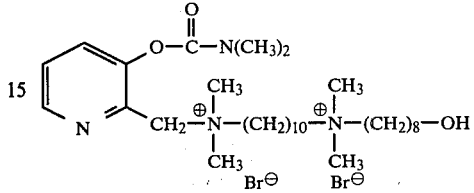

1-[N,N-diethyl-N-(2-hydroxy)ethylammonio]-10-[N-(3-dimethylcarbamoxy-α-picolinyl)-N,N-dimethylammonio]-decane dibromide.

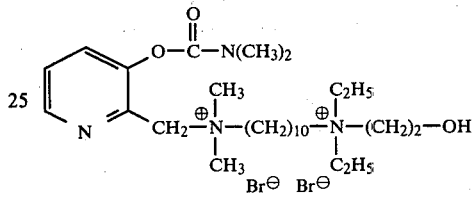

1-[N,N-dipropyl-N-(2-hydroxy)ethylammonio]-10-[N-(3-dimethylcarbamoxy-α-picolinyl)-N,N-dimethylammonio]-decane dibromide.

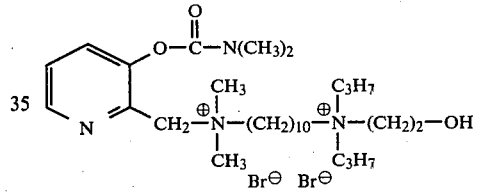

1-[N,N-dipropyl-N-(3-hydroxy)propylammonio]-10-[N-(3-dimethylcarbamoxy-α-picolinyl)-N,N-dimethylammonio]-decane dibromide.

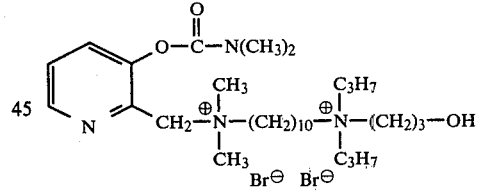

1-[N,N-dimethyl-N-(1,1-dimethyl-2-hydroxy)ethylammonio]-10[N-(3-dimethylcarbamoxy-α-picolinyl)-N,N-dimethylammonio] decane dibromide.

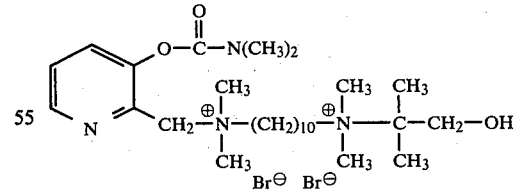

1-[N,N-dimethyl-N-(1,1-diethyl-2-hydroxy)ethylammonio]-10-[N-(3-dimethylcarbamoxy-α-picolinyl)-N,N-dimethylammonio] decane dibromide.

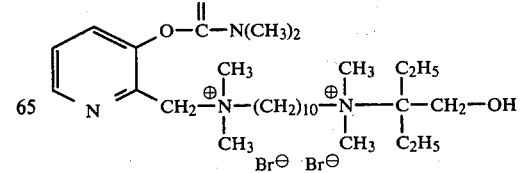

1-[N,N-dimethyl-N-(2-hydroxy)propylammonio]-10-[N-(3-

-continued
dimethylcarbamoxy-α-picolinyl)-N,N-dimethylammonio]-decane dibromide.

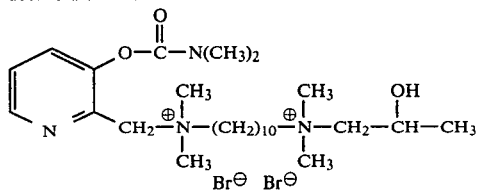

1-[N,N-diethyl-N-(3-hydroxy-4-ethyl)heptylammonio]-10-[N-(3-dimethylcarbamoxy-α-picolinyl)-N,N-dimethylammonio]decane dibromide.

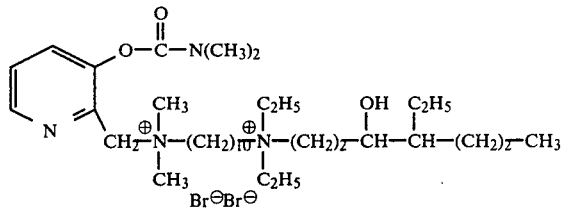

1-[N,N-di(2-hydroxyethyl)-N-methylammonio]-10-[N-(3-dimethylcarbamoxy-α-picolinyl)-N,N-dimethylammonio]decane dibromide.

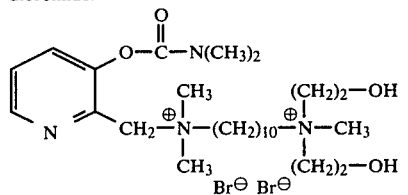

1-[N,N,N-tri(2-hydroxy)ethylammonio]-10-[N-(3-dimethylcarbamoxy-α-picolinyl)-N,N-dimethylammonio]decane dibromide.

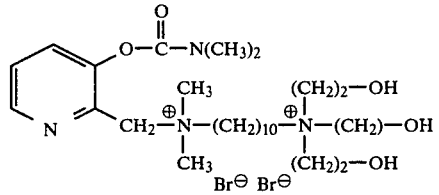

1-[N,N-dimethyl-N-(1-methyl-2-(hydroxy)ethylammonio]-10-[N-(3-dimethylcarbamoxy-α-picolinyl)-N,N-dimethylammonio]decane dibromide.

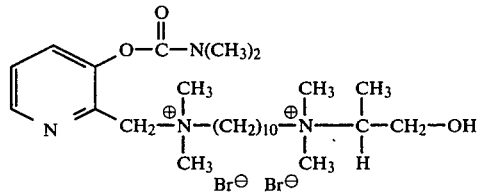

We have shown preferred compounds in which the anion is limited to the halogen moiety, in particular the bromide, since the bromoalkanes are good quaternizing agents. In general, however, it is only necessary that the anions merely have to meet the requirement of being capable of forming a stable salt with the quaternary nitrogen. Thus, the halogen ions can be exchanged with other anions of relatively strong monovalent or polyvalent acid by conventional methods. For example, if $X^-$ is a bromide in the final product, a solution of the compound can be treated with a basic ion exchange resin or mixed with silver oxide and subsequently the desired acid is added to the quaternary hydroxide solution. Anions other than halogens may also be obtained by metathesis with the halide form of the quaternary ammonium compound. Suitable as representations of $X^-$ are the anions hydrogen oxalate, perchlorate, nitrate, tetraphenylboronate, hydrogen sulfate. Representative examples of these additional endproducts are:

1-[N,N-dimethyl-N-(3-hydroxy)propylammonio]-10-[N-(3-dimethylcarbamoxy-α-picolinyl)-N,N-dimethylammonio]decane di(hydrogen oxalate).

1-[N,N-dimethyl-1-N-(3-hydroxy)propylammonio]-10-[N-(3-dimethylcarbamoxy-α-picolinyl)-N,N-dimethylammonio]decane diperchlorate.

1-[N,N-dimethyl-N-(3-hydroxy)propylammonio]-10-[N-(3-dimethylcarbamoxy-α-picolinyl)-N,N-dimethylammonio]decane dinitrate.

1-[N,N-dimethyl-N-(3-hydroxy)propylammonio]-10-[N-(3-dimethylcarbamoxy-α-picolinyl)-N,N-dimethylammonio]decane di(tetraphenylboronate).

1-[N,N-dimethyl-N-(3-hydroxy)propylammonio]-10-[N-(3-dimethylcarbamoxy-α-picolinyl)-N,N-dimethylammonio]decane di(hydrogen sulfate).

We claim:

1. New chemical compounds having the generic formula:

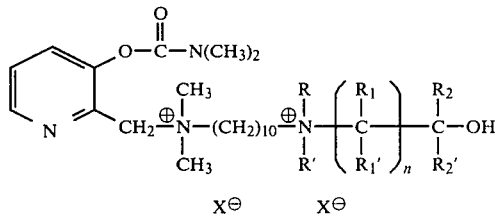

wherein R and R' are aliphatic radicals selected from the group consisting of methyl, ethyl, propyl, and hydroxyethyl; $R_1$ and $R_1'$ are selected from the group consisting of hydrogen, methyl, and ethyl; n is selected from 1–8; $R_2$ and $R_2'$ are selected from the groups consisting of hydroxyl, hydrogen, methyl, and propyl; and X is one equivalent of an anion selected monovalent and polyvalent anions, said anions being selected from the group consisting of halide, hydrogen oxalate, perchlorate, hydrogen sulfate, nitrate, and tetraphenylboronate.

2. New chemical compounds selected from the group of compounds having the names:

1-[N,N-dimethyl-N-(2-hydroxy)ethylammonio]-10-[N-(3-dimethylcarbamoxy-α-picolinyl)-N,N-dimethylammonio]decane dibromide;

1-[N,N-dimethyl-N-(3-hydroxy)propylammonio]-10-[N-(3-dimethylcarbamoxy-α-picolinyl)-N,N-dimethylammonio]decane dibromide;

1-[N,N-dimethyl-N-(6-hydroxy)hexylammonio]-10-[N-(3-dimethylcarbamoxy-α-picolinyl)-N,N-dimethylammonio]decane dibromide;

1-[N,N-diethyl-N-(2-hydroxy)ethylammonio]-10-[N-(3-dimethylcarbamoxy-α-picolinyl)-N,N-dimethylammonio]decane dibromide;

1-[N,N-dimethyl-N-(2-hydroxy)propylammonio]-10-[N-(3-dimethylcarbamoxy-α-picolinyl)-N,N-dimethylammonio]decane dibromide;

1-[N,N-dimethyl-N-(1,1-dimethyl-2-hydroxy)ethylammonio]-10-[N-(3-dimethylcarbamoxy-α-picolinyl)-N,N-dimethylammonio]decane dibromide;

1-[N,N-di(2-hydroxyethyl)-N-methylammonio]-10-[N-(3-dimethylcarbamoxy-α-picolinyl)-N,N-dimethylammonio]decane dibromide;

1-[N,N,N-tri(2-hydroxy)ethylammonio]-10-[N-(3-dimethylcarbamoxy-α-picolinyl)-N,N-dimethylammonio]decane dibromide.

* * * * *